(12) United States Patent
McMorrow et al.

(10) Patent No.: US 7,758,605 B2
(45) Date of Patent: Jul. 20, 2010

(54) BALLOON FOLDING APPARATUS, METHODS AND PRODUCTS

(75) Inventors: David McMorrow, Galway (IE); Anthony O'Brien, Galway (IE); Henrik Hansen, Galway (IE); Thomas McHale, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1625 days.

(21) Appl. No.: 10/851,267

(22) Filed: May 21, 2004

(65) Prior Publication Data

US 2004/0215227 A1    Oct. 28, 2004

Related U.S. Application Data

(63) Continuation-in-part of application No. 10/087,303, filed on Feb. 28, 2002.

(51) Int. Cl.
*A61M 29/00* (2006.01)
(52) U.S. Cl. ...................................... 606/191
(58) Field of Classification Search ................ 606/191, 606/192, 194; 604/96.01, 103.06–103.08, 604/103.14
See application file for complete search history.

(56) References Cited

U.S. PATENT DOCUMENTS

| | | | |
|---|---|---|---|
| 5,049,131 A * | 9/1991 | Deuss | 604/98.01 |
| 5,091,205 A | 2/1992 | Fan | 427/2 |
| 5,147,302 A * | 9/1992 | Euteneuer et al. | 604/103 |
| 5,318,587 A | 6/1994 | Davey | 606/194 |
| 5,320,634 A * | 6/1994 | Vigil et al. | 606/159 |
| 5,350,361 A | 9/1994 | Tsukashima et al. | 604/96 |
| 5,490,839 A | 2/1996 | Wang et al. | 604/96 |
| 5,693,014 A | 12/1997 | Abele et al. | 604/96 |
| 5,720,726 A | 2/1998 | Marcadis et al. | 604/96 |
| 5,738,901 A | 4/1998 | Wang et al. | 427/2.3 |
| 5,746,745 A | 5/1998 | Abele et al. | 606/108 |
| 5,759,172 A * | 6/1998 | Weber et al. | 604/103.07 |
| 5,783,227 A | 7/1998 | Dunham | 425/318 |
| 5,792,172 A | 8/1998 | Fischell et al. | 606/198 |
| 5,893,868 A | 4/1999 | Hanson et al. | 606/198 |
| 5,976,181 A | 11/1999 | Whelan et al. | 623/1 |
| 6,010,480 A | 1/2000 | Abele et al. | 604/96 |
| 6,013,092 A | 1/2000 | Dehdashtiam et al. | 606/194 |
| 6,033,380 A | 3/2000 | Butaric et al. | 604/96 |
| 6,126,652 A | 10/2000 | McLeod et al. | 606/1 |
| 6,176,849 B1 | 1/2001 | Yang et al. | 604/265 |
| 2001/0037140 A1* | 11/2001 | Gaudoin et al. | 623/1.11 |
| 2002/0163104 A1 | 11/2002 | Motsenbocker et al. | 264/320 |
| 2003/0163157 A1 | 8/2003 | McMorrow | 606/194 |

FOREIGN PATENT DOCUMENTS

EP    0 565 799 A 1    11/1992

\* cited by examiner

*Primary Examiner*—Anhtuan T Nguyen
*Assistant Examiner*—Ryan J Severson
(74) *Attorney, Agent, or Firm*—Vidas, Arrett & Steinkraus

(57) ABSTRACT

A medical balloon may be configured by at least partially inflating the medical balloon and forming at least one primary wing in the balloon. The primary wing extends from a central portion of the balloon. The primary wing may be manipulated to form a T-shaped wing therefrom. The balloon may then be deflated and the T-shaped wings wrapped around the balloon.

55 Claims, 20 Drawing Sheets

BALLOON FOLDING APPARATUS, METHODS AND PRODUCTS

CROSS-REFERENCE TO RELATED APPLICATIONS

This is a continuation-in-part of copending U.S. patent application Ser. No. 10/087,303 filed Feb. 28, 2002, the entire content of which is incorporated by reference herein.

BACKGROUND OF THE INVENTION

Medical balloons are used in the body in a variety of applications including as dilatation devices for compressing plaque and for expanding prosthetic devices such as stents at a desired location in a bodily vessel. Because it is typically necessary for the balloon to traverse a tortuous anatomy as it is being delivered to the location in a bodily vessel, it is desirable for the balloon to assume as low a profile as possible.

One way to achieve a low profile is by folding the balloon to form a number of wings. Current technologies typically employ a number of hard dies, which are moved radially inward toward the center of a partially inflated balloon. The balloon is maintained in a partially inflated state until the dies have reached the end of their stroke. A vacuum is then applied to the balloon to deflate the balloon and form wings that conform to the configuration of the dies. The wings may then be wrapped or rolled around the circumference of the balloon. This method is not effective, however, for forming wings with undercuts or multiple layers.

Where a balloon with wrapped wings is used to expand a stent, a rotational moment is imparted on the stent as a result of the unfolding of the wings as the balloon expands. The interaction between the stent and the balloon may cause undesirable wear to the stent and/or balloon. Where the stent comprises a coating, the rotational movement may damage the coating and may damage the wall of the vessel in which the stent is located.

Balloons with rolled wings also exhibit non-circular, irregular cross-sections. The irregular cross-section can facilitate contact between adjacent struts of a crimped-on stent. This contact can, in turn, lead to bonding between adjacent struts on coated stents when the stent is sterilized and the coating softens.

There remains a need for innovative methods for folding balloons, which avoid some of the problems that may result, in certain circumstances, from balloons having rolled wings. There also remains a need for innovative methods for folding balloons, in particular where multi-layer folds are desired.

All U.S. patents and applications and all other published documents mentioned anywhere in this application are incorporated herein by reference in their entirety.

Without limiting the scope of the invention a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

SUMMARY OF THE INVENTION

In one embodiment, the invention is directed to a method of configuring medical balloon catheter assembly comprising the steps of providing a medical balloon, at least partially inflating the medical balloon, forming a plurality of primary lobes extending from a central portion of the balloon and spaced about the periphery of the balloon and manipulating at least one primary lobe to form at least two secondary lobes therefrom. Finally, the balloon is deflated.

The primary lobes may be formed by applying a radially inward force to the balloon at one or more locations. A plurality of first impinging members spaced about the periphery of the balloon may be directed radially inward to apply the radially inward force to the balloon.

Some or all of the primary lobes may be manipulated so as to form at least two adjacent secondary lobes from each primary lobe that has been manipulated. Desirably, a radially inward force is applied to each primary lobe during the manipulating step to form a pair of secondary lobes from each primary lobe. A plurality of second impinging members spaced about the periphery of the balloon may be directed radially inward to apply the radially inward force to the primary lobes and form the secondary lobes.

Some or all of the primary lobes may also be manipulated to form at least three secondary lobes. This may be accomplished by a variety of methods including by impinging two or more second impinging members inward against each primary lobe. In one embodiment of the invention, a first secondary lobe, a second secondary lobe and a third secondary lobe are formed from each primary lobe. The first secondary lobe is larger than the second secondary lobe and the third secondary lobe.

The inventive method may further comprise the step of applying a vacuum to the balloon following formation of the secondary lobes to deflate the balloon. Optionally, depending on how many secondary lobes are formed from each primary lobe during the deflating step, a plurality of antenna-shaped structures extending from a central portion of the balloon may be formed. Each antenna-shaped structure includes a center antenna portion extending outward from the balloon and a plurality of wings extending from a first side of the center antenna portion and a plurality of wings extending from a second side of the center antenna portion opposite the first side. In one embodiment, the antenna-shaped structure includes two wings extending from the first side of the central portion of the balloon and two wings extending from the second side of the central portion of the balloon.

In another aspect, the invention relates to a method in which a medical balloon catheter assembly is configured by providing a medical balloon catheter assembly including a medical balloon, at least partially inflating the medical balloon, forming a plurality of primary wings in the balloon, then deflating the balloon, the wings spaced about the periphery of the balloon and extending from a central portion of the balloon, at least partially reinflating the medical balloon such that the primary wings form lobes, and manipulating the lobes to form a plurality of T-shaped wings and then deflating the medical balloon. A vacuum may be applied to deflate the balloon during formation of the primary and secondary T-shaped wings.

The primary wings may be formed by first impinging members and the secondary T-shaped wings may be formed by second impinging members which may be the same as or different than the first impinging members.

In one embodiment, the second impinging members are different than the first impinging members in that the first impinging members have a conical or V-shaped tip or edge that comes into contact with the balloon and the second impinging members have a flat edged tip which comes into contact with the balloon.

The tips of the impinging members in any of the embodiments described above may be "soft tipped". The soft tip may be polymeric. In one embodiment, the soft tip is formed from silicone. The body of the impinging members may be metallic and the silicone coated or otherwise adhered to the body of the impinging members.

In one embodiment, the resultant balloon has T-shaped wings. Desirably, the balloon has at least two T-shaped wings and in one embodiment, the balloon has three T-shaped wings. However, balloon may have 4, 5, 6 and so forth T-shaped wings as well. Each T-shaped wing is formed from the primary wing which in turn becomes a lobe or smaller balloon portions upon reinflation of the balloon to at least a partially inflated state.

The present invention also relates to the apparatus for forming the above described balloon, the apparatus including impinging members as described above. The apparatus includes a catheter holder, a plurality of movable blades or impinging members disposed about a common central point and one or more blade moving devices in mechanical communication with the movable blades, the one or more blade moving devices is capable of moving the movable blades inward toward the common central point. The apparatus may include a first set of blades with a conical or V-shaped tip and a second set of blades with a flat edged tip which comes into contact with the balloon. The apparatus desirably has two or more blades in the first set and two or more blades in the second set. In one embodiment, the apparatus has three or more blades in the first set and three or more blades in the second set, but may have 4, 5, 6 or more blades in each set as well. Any or all of the blades may have a soft-tipped construction.

The inventive method may optionally comprise the further step of wrapping the deflated secondary lobes or the secondary T-shaped wings about the central portion of the balloon. Desirably, secondary lobes that are formed from the same primary lobe are wrapped in opposite directions from one another about the central portion of the balloon. This may be accomplished, for example, by wrapping every other secondary lobe in a first direction about the central portion of the balloon and subsequently wrapping any unwrapped lobes in a second direction opposite the first direction about the central portion of the balloon.

Upon completion of the wrapping of the balloon, desirably each pair of secondary lobes includes a first secondary lobe, which overlaps, with one secondary lobe from an adjacent pair of secondary lobes and a second secondary lobe, which is overlapped by one secondary lobe from another adjacent pair of secondary lobes.

The wrapping of the balloon may be accomplished through a variety of methods including by using a plurality of third impinging members to apply a force to every other secondary lobe. Desirably, the force will be directed toward the central portion of the balloon. A plurality of fourth impinging members may then be used to apply a force to every remaining unwrapped lobe to wrap the remaining lobes. Desirably, the force will be directed toward the central portion of the balloon.

In another embodiment, the invention is also directed to a method of forming balloon wings in a medical balloon comprising the steps of providing a medical balloon with one or more primary lobes therein, forming a plurality of secondary lobes from each primary lobe by applying an inward force to each of the primary lobes and deflating the balloon. Desirably, the inward force is applied to the primary lobes via a plurality of impinging members. The impinging members may be removed following the forming step by optionally moving the impinging members in an axial direction.

In another embodiment, the invention is also directed to the combination of a medical balloon and an expandable prosthetic device disposed about the medical balloon. The medical balloon comprises a plurality of wings extending from a main balloon body, the wings wrapped about the main balloon body such that upon inflation of the medical balloon there is substantially no relative rotational movement between the prosthetic device and the balloon.

In another embodiment, the invention is also directed to a medical balloon having a central portion and a plurality of wings disposed thereabout, the plurality of wings including at least one first wing wrapped in a first direction about the central portion of the balloon and at least one second wing wrapped in a second direction opposite the first direction about the central portion of the balloon. Desirably, the balloon comprises a plurality of first wings wrapped in the first direction about the central portion of the balloon and a plurality of second wings wrapped in the second direction about the central portion of the balloon. The first and second wings alternate with one another about the central portion of the balloon.

In another embodiment, the invention is also directed to a medical balloon comprising a central portion and a plurality of structures extending from the central portion, each structure having a first wing extending therefrom in a first direction and a second wing extending therefrom in a second direction opposite the first direction. Typically, the structures are in the form of a T-shaped structure or a V-shaped structure. Optionally, the structures may be spaced apart such that each secondary wing is in an overlapping relationship with one first wing.

In another embodiment, the invention is also to the combination of the inventive balloons disclosed herein and a prosthetic device, such as, for example, a stent disposed about the medical balloon. The prosthetic device may include a coating comprising a therapeutic agent.

In another embodiment, the invention is also directed to the combination of a medical balloon and an expandable prosthetic device disposed about the medical balloon where the medical balloon comprising a plurality of wings extending from a main balloon body. The wings are wrapped about the main balloon body such that upon inflation of the medical balloon there is substantially no relative rotational movement between the prosthetic device and the balloon.

The invention is also directed to an apparatus for configuring a medical balloon of a medical balloon catheter assembly. The apparatus comprises a catheter holder, a plurality of movable blades disposed about a common central point and one or more blade moving devices in mechanical communication with the movable blades, the one or more blade moving devices is capable of moving the movable blades inward toward the common central point.

Additional details and/or embodiments of the invention are discussed below.

DETAILED DESCRIPTION OF THE INVENTION

Figure 1:
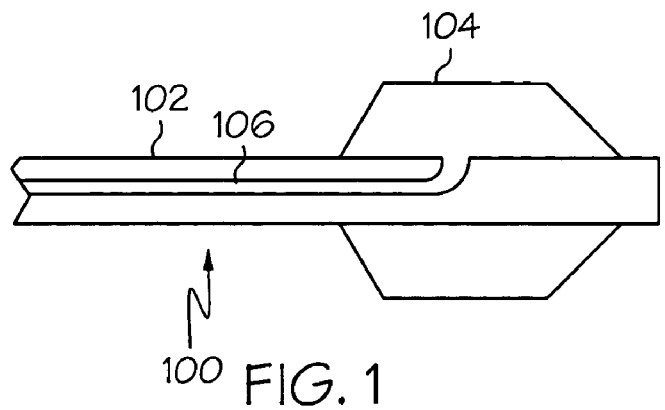
FIG. 1 shows a longitudinal cross-section of a portion of a balloon catheter assembly.

While this invention may be embodied in many different forms, there are shown in the drawings and described in detail herein specific embodiments of the invention. The present disclosure is an exemplification of the principles of the invention and is not intended to limit the invention to the particular embodiments illustrated.

For the purposes of this disclosure, like reference numerals in the figures shall refer to like features unless otherwise indicated.

In one embodiment, the invention is directed to a method of configuring a medical balloon catheter assembly such as that shown generally at 100 in FIG. 1. Medical balloon catheter assembly comprises catheter tube 102 and medical balloon 104 disposed thereabout. Inflation lumen 106 is in fluid communication with medical balloon 104. As shown in FIG. 1, inflation lumen 106 is disposed within catheter tube 102. The inflation lumen may also be provided in the form of a dual lumen tube, one lumen of which is in fluid communication with the balloon. Any other suitable arrangement may also be used for the inflation lumen.

Figure 2:
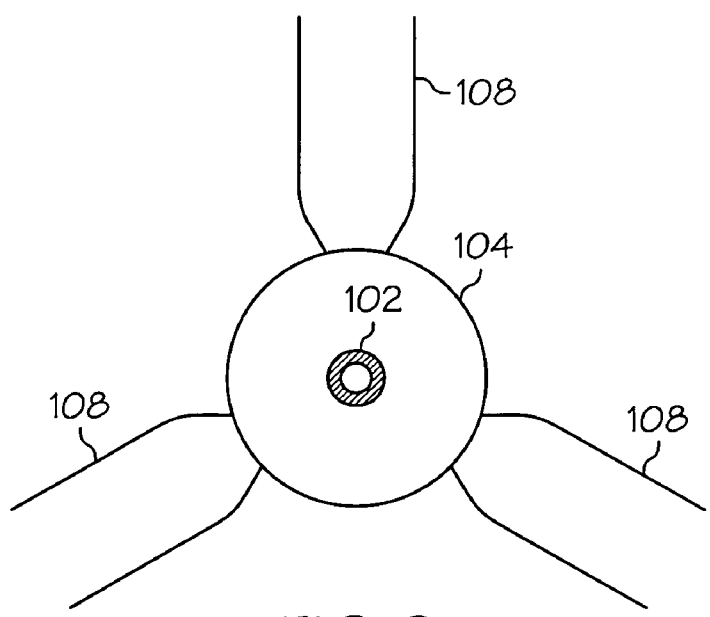
FIG. 2 is a transverse cross-section of a balloon catheter assembly with the balloon at least partially inflated.
Figure 3:
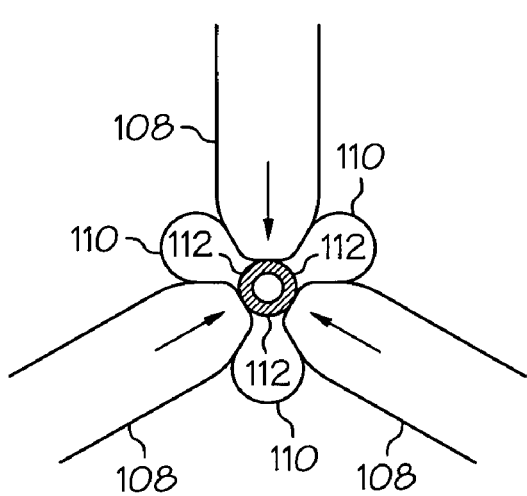
FIG. 3 is a transverse cross-section of a balloon catheter assembly with primary lobes formed therein.

In accordance with one embodiment of the invention, as shown in FIG. 2, medical balloon 104 is at least partially inflated and, optionally, fully inflated. At least one, and desirably, a plurality of first impinging members 108 are disposed about medical balloon 104. Typically, first impinging members 108 will have a relatively wide balloon contacting surface. First impinging members 108 are directed inward to form a plurality of primary lobes 110 as shown in FIG. 3. Desirably, primary lobes 110 are spaced regularly about the periphery of the balloon and extend from central portion 112 of the balloon. In the embodiment of 2 and 3, a balloon with three primary lobes is shown by way of non-limiting example. Typically, the balloon will be manipulated to have four, five, six, seven, eight, nine, ten or more primary lobes. More generally, the balloon may be manipulated to provide at least two primary lobes.

For purposes of this application, the term "impinging member" may be used interchangeably with "blade".

Figure 4:
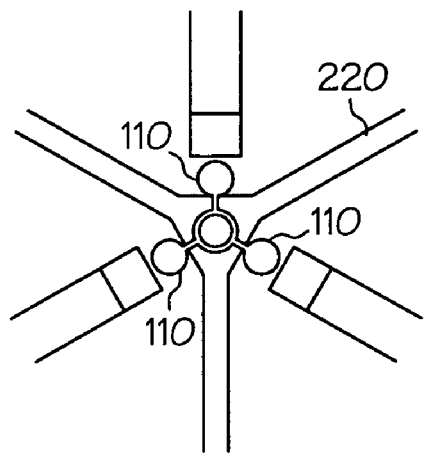
FIGS. 4-6 are transverse cross-sections of a balloon catheter assembly during the formation of secondary lobes.
Figure 5:
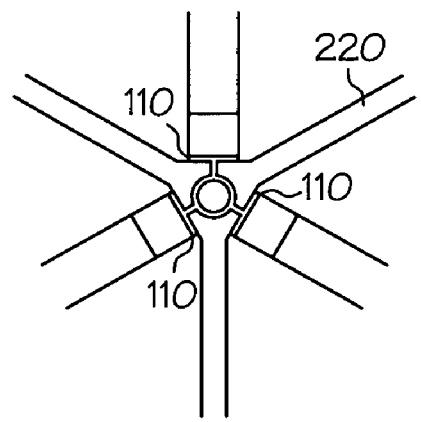

As shown in FIG. 4, at least one and desirably a plurality of second impinging members 114 are disposed against primary lobes 110, desirably at the middle of the lobes. Typically, second impinging members 114 will have a relatively narrow balloon contacting surface as compared with first impinging members 108. A radially inward force is applied to at least one of the primary lobes by second impinging members 114 so as to form at least two secondary lobes 116a and 116b from the primary lobe 110, as shown in FIG. 5.

Figure 6:
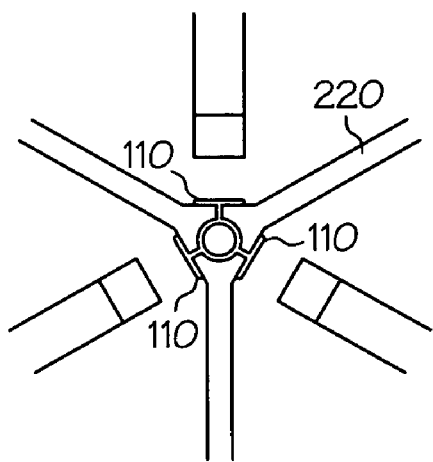
Figure 7:
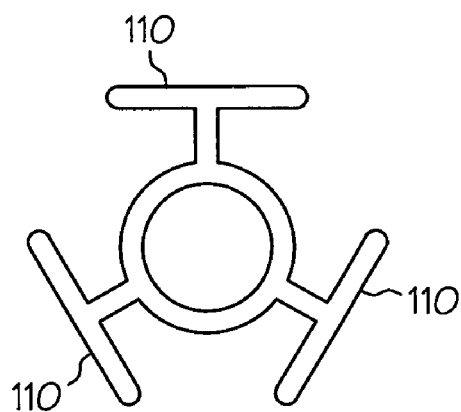
FIG. 7 is a transverse cross-section of a V-formed balloon catheter assembly.

Balloon 104 is then at least partially and desirably fully deflated by applying a vacuum thereto to collapse inward and form collapsed lobes or wings 118a and 118b corresponding to secondary lobes 116a and 116b as shown in FIGS. 6 and 7.

Figure 8:
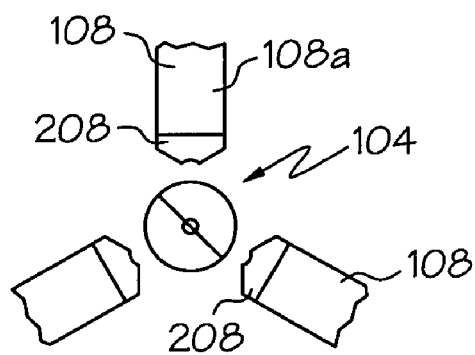
FIGS. 8-18 are transverse cross-sections of a balloon catheter assembly during the formation of secondary lobes using an inventive process.

Another process is illustrated in FIGS. 8-18. FIG. 8 shows a cross-sectional end view of balloon 104 in an at least partially inflated configuration using a pressure of about 30 psi with impinging members 108 being moved radially forward toward the balloon 104. The range for the pressure employed may be from about 1 psi to about 30 psi. In this embodiment the impinging members 108 are shown with a soft-tipped configuration with tips 208 formed from or coated with a polymeric composition such as silicone, for example, while the body 108a of impinging member 108 may be formed of a metal, for example. Tips may be formed from both polymeric materials as well as metals. Examples include, but are not limited to, polyurethane, polyethylene, stainless steel, and so forth.

Figure 9:
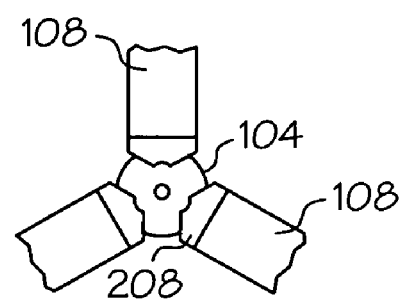

FIG. 9 shows the impinging members 108 moved forward to contact balloon 104.

Figure 10:
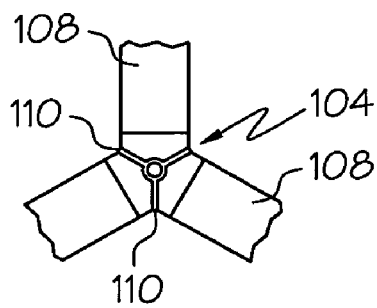
Figure 11:
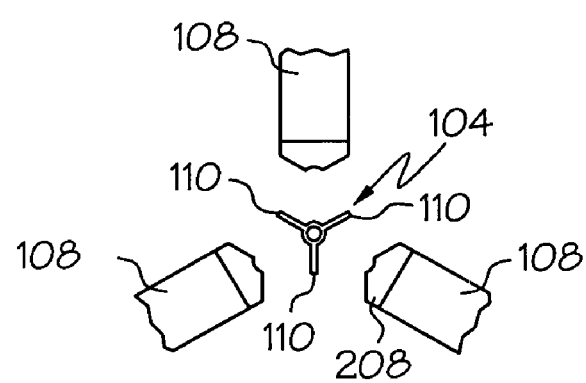
Figure 12:
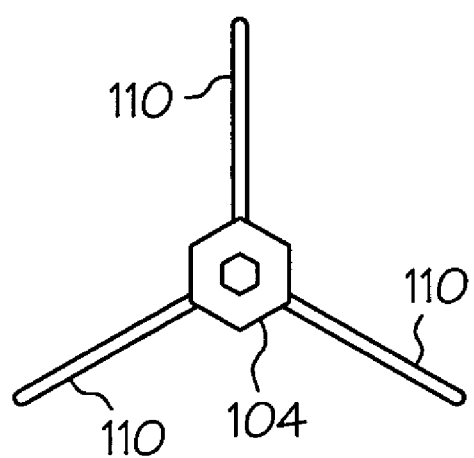

In FIG. 10, the impinging members 108 have been moved fully forward and into position to form three primary lobes. This configuration is shown by way of non-limiting example. The balloon can be manipulated to have any of a number of lobes including, four, five, six, seven, eight, nine, ten or more primary lobes. More generally, the balloon may be manipulated to provide at least two primary lobes. Following the procedure, a vacuum is drawn and the impinging members 108 retracted as shown in FIG. 11. FIG. 12 shows the three winged balloon structure formed at this point in the process, the balloon shown in a deflated configuration.

Figure 13:
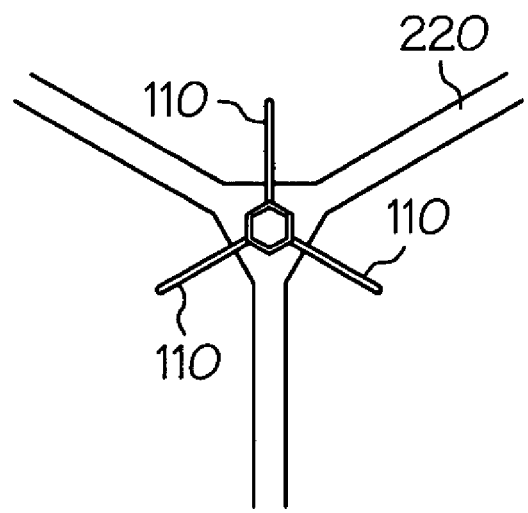

The balloon may then be retained on a holding structure 220 as shown in FIG. 13 wherein the wings are accessible to the secondary impinging members 114a.

Figure 14:
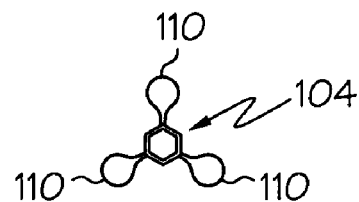
Figure 15:
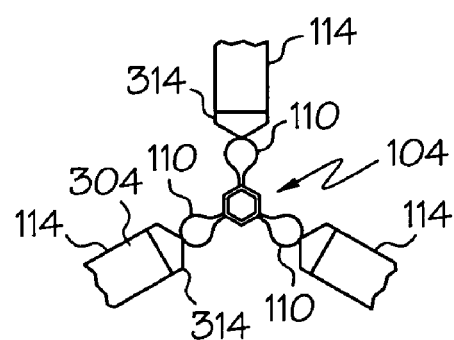

In this process, the balloon can then be reinflated as shown in FIG. 14, shown with three primary lobes 110 or smaller balloon portions. Balloon 104 is at least partially reinflated with a relatively lower pressure than that used initially as shown in FIG. 8, such as about 15 psi, although this may be varied from about 1 psi to about 30 psi. Second impinging members 114, are then moved toward inflated balloon lobes 110 as shown in FIG. 15. In this configuration, the balloon tips 314 have a conical or V shape configuration and again, the impinging members 114 have the soft-tipped configuration. From this point, the balloon can be manipulated to form a structure similar to that previously shown in FIGS. 6 and 7 described above.

Figure 16:
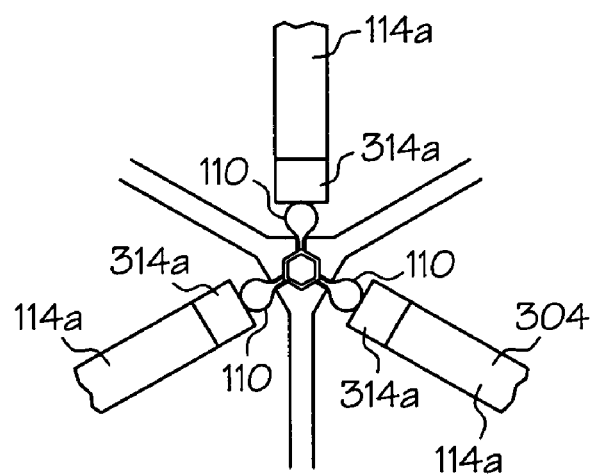
Figure 17:
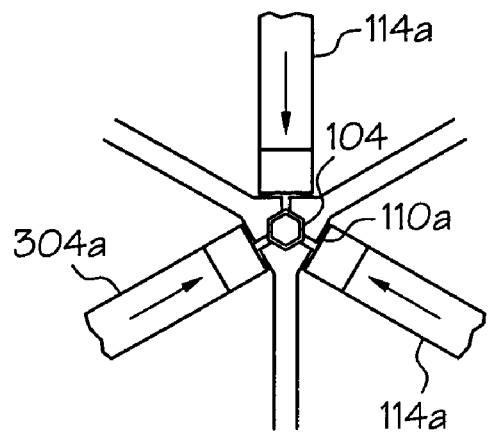
Figure 18:
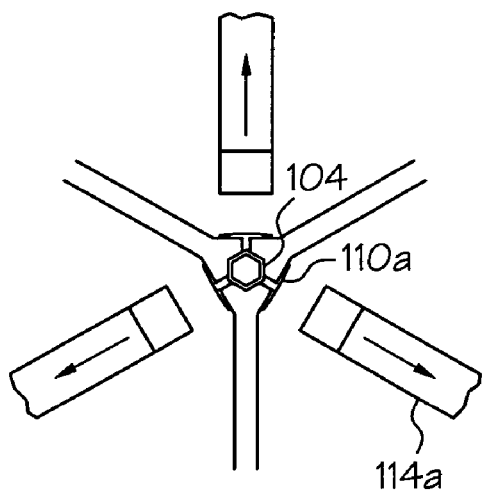
Figure 19:
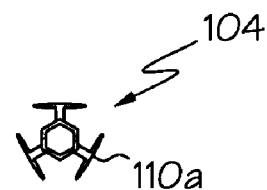
FIG. 19 is a transverse cross-section of a T-formed balloon catheter assembly prior to wrapping the wings.

It is also within the scope of the invention for impinging members 114*a* to have a flat tipped configuration as shown in FIG. 16. Manipulation of the balloon using the flat-tipped configuration is shown in FIG. 17, wherein the impinging members 114*a* having fully contacted and manipulated balloon wings 110*a*, forming them into a T-shaped structure. Again, in this embodiment, the impinging members 114*a* have a body portion 304*a* and a soft-tipped portion 314*a*. The inward radial movement of these soft-tipped blades flatten the lobe 110*a* on the wing tip. A vacuum is applied and the impinging members 114*a* are shown being withdrawn from balloon 104 as shown in FIG. 18. FIG. 19 shows the T-shaped structure of the balloon.

Figure 20:
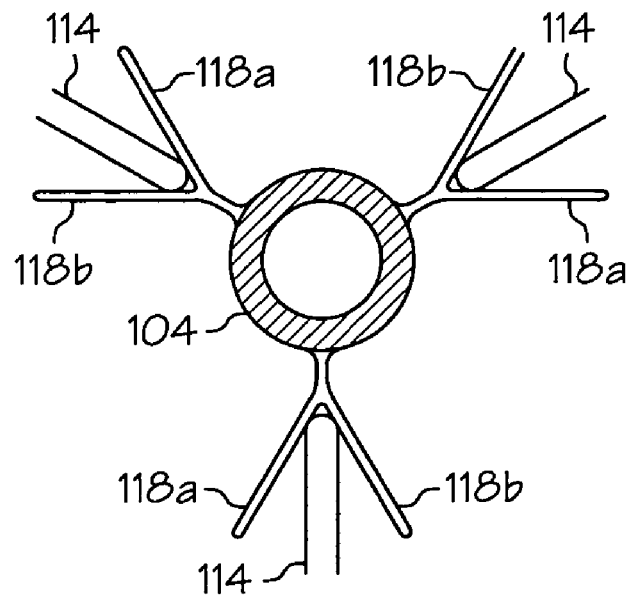
FIG. 20 is a transverse cross-section of a V-formed balloon catheter assembly prior to wrapping the wings.

The inventive V-formed balloon of FIGS. 6 and 7 or the inventive T-formed balloons of FIG. 19 may be wrapped in a number of different ways. One method of wrapping the V-formed balloon is shown in FIGS. 20-23. As shown in FIG. 20, first impinging members 108 are removed from contact with the balloon. Second impinging members 114 may be left in place or removed and replaced by other impinging members. A plurality of third impinging members 120 are brought into contact with secondary wings 118*a* and a plurality of fourth impinging members 122 are brought into contact with secondary wings 118*b*.

Figure 21:
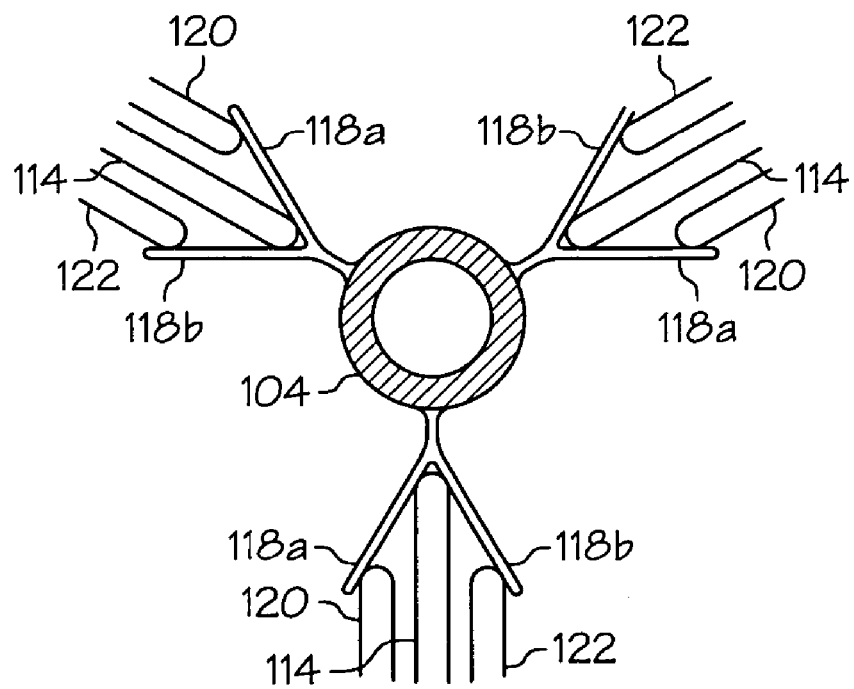
FIGS. 21-23 are transverse cross-sections of a balloon catheter assembly illustrating the wrapping of the wings.
Figure 22:
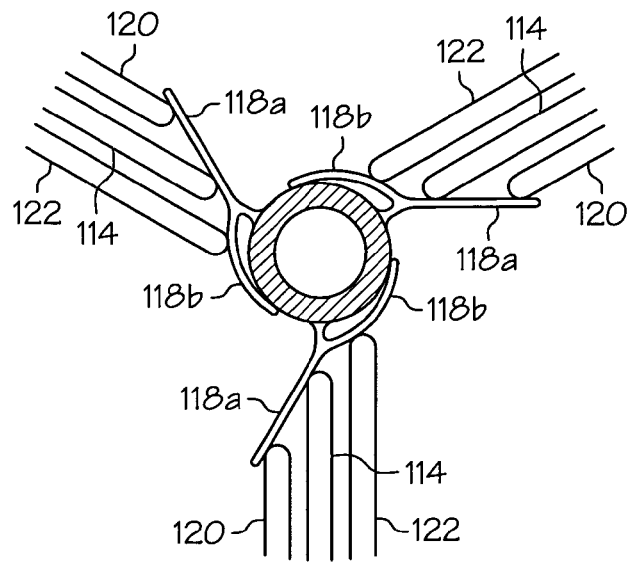

Fourth impinging members 122 are moved inward relative to balloon 104 as shown in FIG. 21 and secondary wings 118*b* are wrapped in a first direction about the central portion of the balloon. Third impinging members 120 are then moved inward relative to balloon 104 as shown in FIG. 22 and secondary wings 118*a* are wrapped about the central portion of the balloon in a second direction opposite to the first direction. By wrapping secondary wings 118*b* separately from secondary wings 118*a*, the possibility of the secondary wings 118*a* and 118*b* hitting one another during the wrapping steps is eliminated.

As shown in FIGS. 21 and 22, secondary wings 118*b* are wrapped in a counter-clockwise direction first and secondary wings 118*a* are subsequently wrapped in a clockwise direction. It is also within the scope of the invention to first wrap secondary wings 118*a* in a clockwise direction and to subsequently wrap secondary wings 118*b* in a counter-clockwise direction.

The individual secondary wings 118*a* may be wrapped simultaneously with one another or may be wrapped sequentially or in any other sequence. Similarly, individual secondary wings 118*b* may be wrapped simultaneously with one another or may be wrapped sequentially.

It is also within the scope of the invention to wrap one pair of secondary wings in first and second opposing directions and to wrap the other secondary wings in other ways.

Subsequent to wrapping the balloon, all of the impinging members may be removed.

In accordance with the invention, as few as one pair of secondary wings may be formed and wrapped about the central portion of the balloon. In the embodiments shown in FIGS. 13-22, three pairs of secondary wings are formed and wrapped about the central portion of the balloon. Typically, two, three, four, five, six, seven, eight, nine, ten or more pairs of secondary wings will be formed and wrapped about the central portion of the balloon. More generally, a plurality of pairs of secondary wings may be formed and wrapped.

Optionally, after wrapping, a bi-tube or balloon protector may be disposed about the balloon to assure that the balloon does not unwrap. This optional step may be incorporated into any of the embodiments described herein. A bi-tube is a cylindrical hollow tube used to hold balloon folds in place. It has the same basic form and function as a balloon protector, although a balloon protector may have flared ends and are typically shipped with the product.

Figure 23:
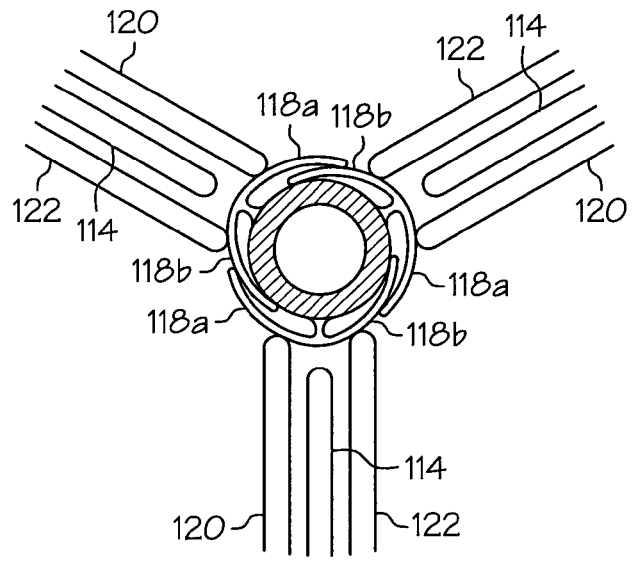

The invention is also directed to a medical balloon such as that shown at 104 in FIG. 23 having a central portion 104 and a plurality of wings disposed thereabout including at least one first wing 118*a* wrapped in a first direction about the central portion of the balloon and at least one second wing 118*b* wrapped in a second direction opposite the first direction about the central portion of the balloon.

Desirably, as shown in FIG. 23, the now T-formed balloon comprises a plurality of first wings 118*a* wrapped in the first direction and a plurality of second wings 118*b* wrapped in second first direction. In the embodiment of FIG. 23, the first and second wings alternate with one another about the central portion of the balloon. The first and second wings form part of a T-shaped structure, shown generally at 124 with hatching, extending from the central portion of the balloon. Each T-shaped structure includes one first wing and one second wing. Desirably, as shown in FIG. 23, each secondary wing 118*b* is in an overlapping relationship with one first wing 118*a*.

The invention is also directed to a medical balloon having a central portion and a plurality of T structures and/or V structures extending from the central portion, the structure having a first wing extending therefrom in a first direction and a second wing extending therefrom in a second direction opposite the first direction. Desirably, as shown in FIG. 23, the balloon comprises a plurality of T-shaped structures 124 extending from central portion 112 of balloon 104.

The invention is further directed to a method of configuring a medical balloon in which multiple secondary lobes are formed from primary lobes using impinging members that apply a non-radially inward force to the primary lobes.

Figure 24:
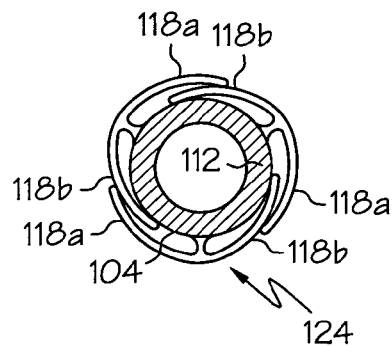
FIG. 24 is a transverse cross-section of a balloon with T-wings after wrapping.
Figure 25:
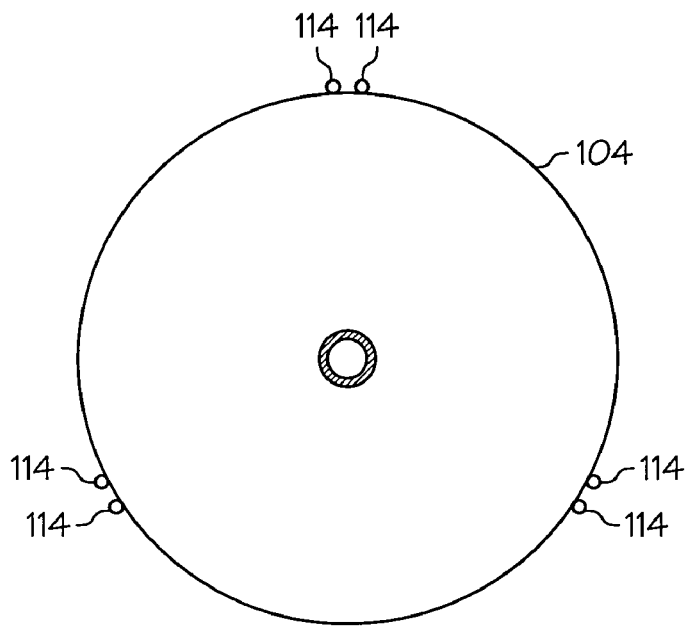
FIG. 25 shows an arrangement of a balloon and a plurality of impinging members prior to the formation of primary lobes.
Figure 26:
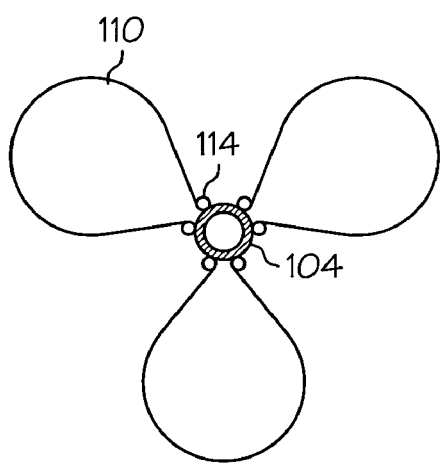
FIG. 26 shows the balloon of FIG. 25 with primary lobes formed therein.

As shown in FIGS. 24 and 25, one or more pairs of impinging members 114 are disposed about the periphery of balloon 104. One or more primary lobes 110 are formed by moving impinging members 114 substantially radially inward. Impinging members 114 are then repositioned or new impinging members are provided, as shown in FIG. 26, on either side of primary lobe 110 and an inward force applied against primary lobe 110 to form three secondary lobes 116*a*-*c*. Desirably, each primary lobe is thus transformed into three secondary lobes. Optionally, as shown in FIG. 26, first secondary lobe 116*b* is larger than second secondary lobe 116*a* and third secondary lobe 116*c*. The first, second and third secondary lobes may also be of the same size as one another. Other size relationships between the first, second and third secondary lobes are also within the scope of the invention.

Figure 36:
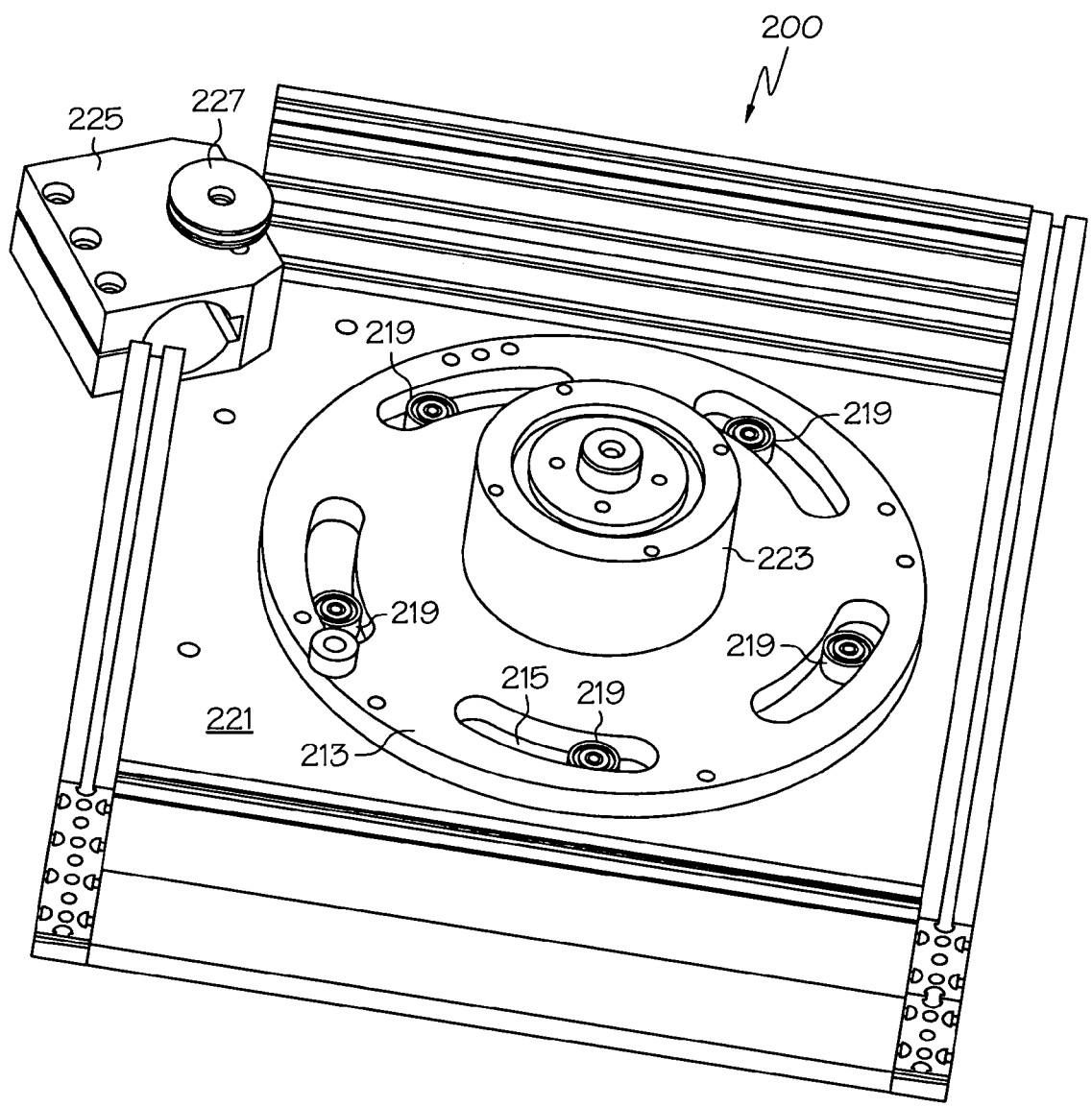
FIG. 36 is an exploded view of the back of the inventive balloon configuring device shown in FIGS. 31-33.
Figure 37:
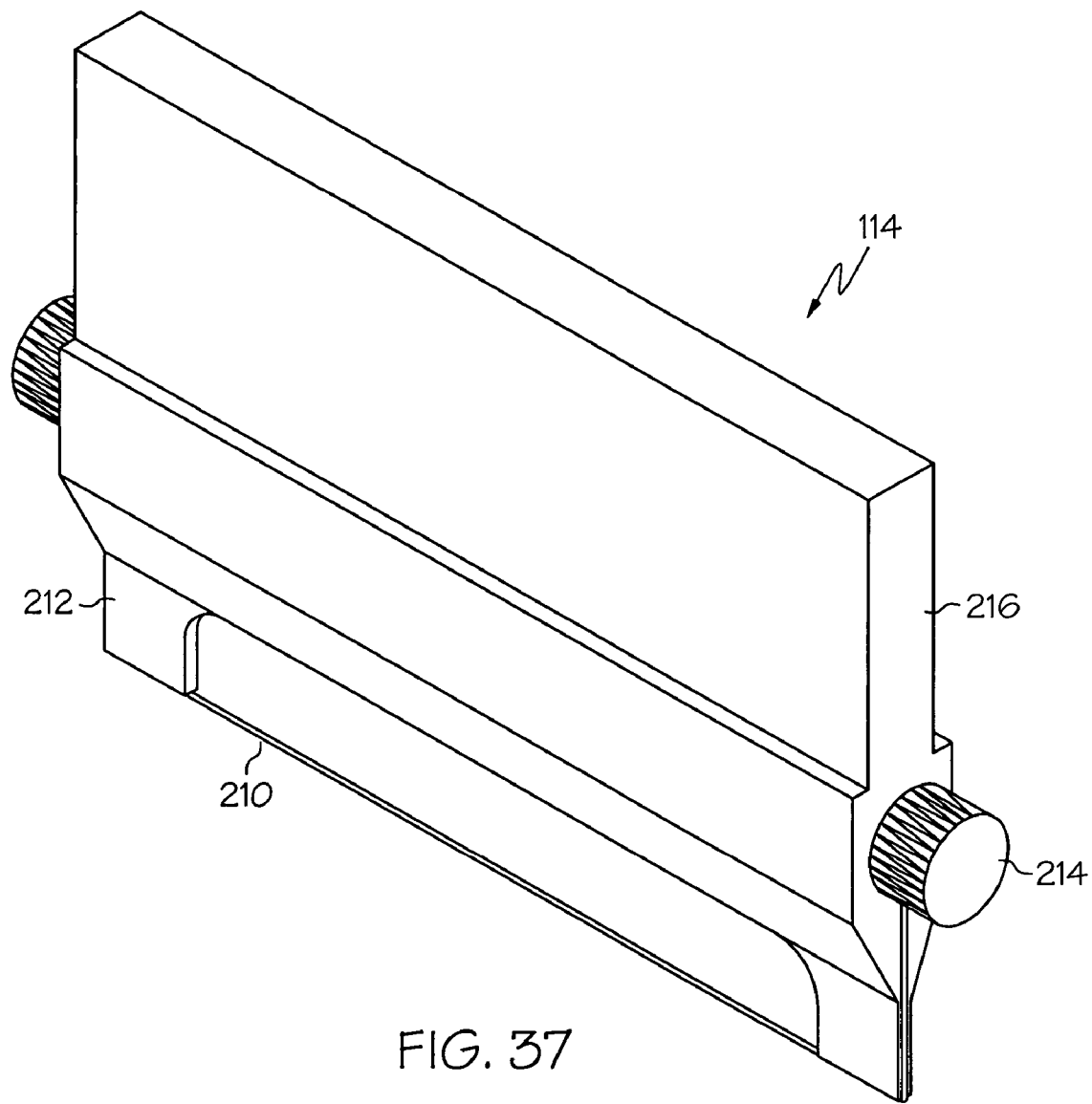
FIGS. 37 and 38 show inventive impinging members which may be used in the device of FIG. 33.

Desirably, impinging members 114 shown in FIGS. 26, 36 and 37 comprise elongate structures such as wires that are held in tension or plastic parisons. The elongate structures may be disposed parallel to the longitudinal axis of the balloon. The required number of elongate structures will depend on how many secondary lobes are to be formed from each primary lobe. Generally, where it is desired to form N lobes from a primary lobe, N−1 elongate structures will be required. The impinging members may also be in the form of bar, rods or any other structure that may be used to apply a force to the balloon without damaging the balloon. Suitably, the impinging members will have a radiused portion that contacts the balloon. The impinging members may be made of metal, polymeric material or any other suitable material. Desirably, second impinging members are removed subsequent to formation of the secondary lobes by moving the secondary impinging members in an axial direction.

The impinging members, when in the form of wires held in tension, may then be removed by releasing one end and pulling or pushing the member in an axial direction.

Figure 27:
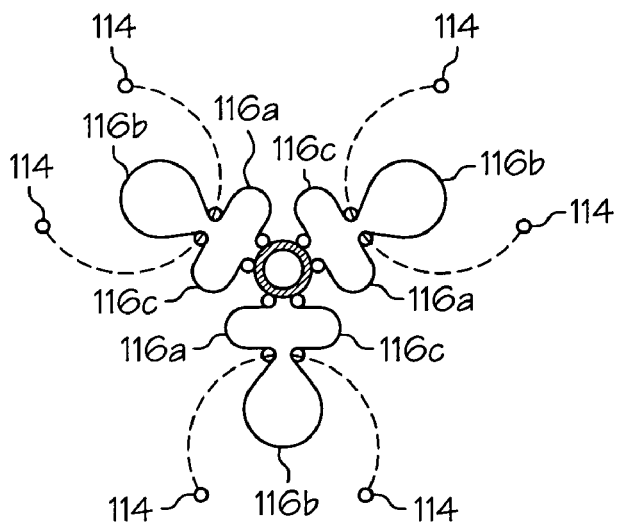
FIG. 27 is a transverse cross-section of a balloon catheter assembly that has been manipulated to form three secondary lobes from every primary lobe.
Figure 28:
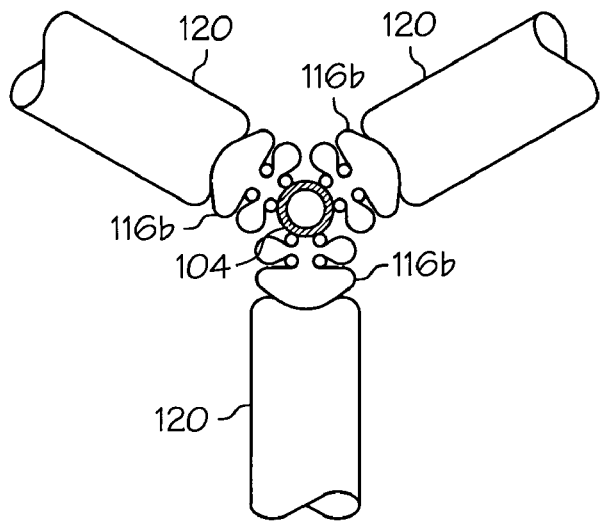
FIG. 28 shows the balloon catheter assembly of FIG. 26 with third impinging members applying a radially inward force to the some of the secondary lobes.
Figure 29:
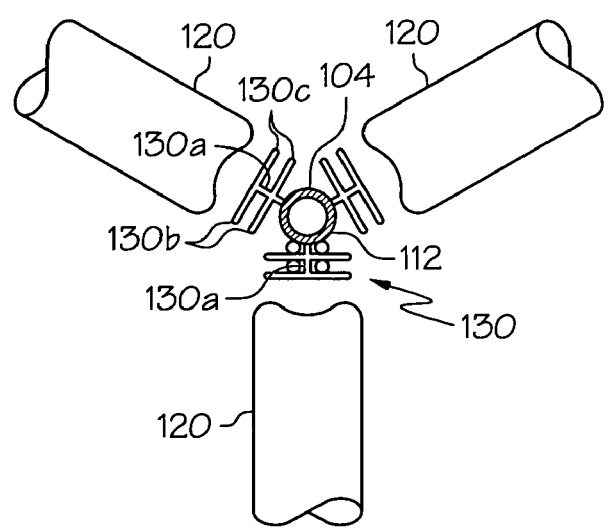
FIG. 29 shows the balloon catheter assembly of FIG. 26 following deflation and the formation of antenna structures.

Balloon 104 may then be deflated, optionally by applying a vacuum thereto. During deflation, as shown in FIG. 27, a plurality of third impinging members 120 may apply a radially inward force to secondary lobes 116b. Typically, third impinging members 120 are in the form of dies having curved faces that match the profile of the balloon. Upon deflation of balloon 104, as shown in FIG. 28, at least one and desirably a plurality of antenna-shaped structures, shown generally at 130, extend from a central portion 112 of the balloon. Desirably, each antenna-shaped structure 130 includes a center antenna portion 130a extending outward from the balloon and a plurality of wings 130b extending from a first side of center antenna portion 130a and a plurality of wings 130c extending from a second side of center antenna portion 130a opposite the first side. Further in accordance with the invention, three or more wings may extend from each side of the center antenna portion.

Antenna structures 130 may then be wrapped about the balloon by applying a radially inward force to each antenna structure 130 using third impinging members 120.

Figure 30:
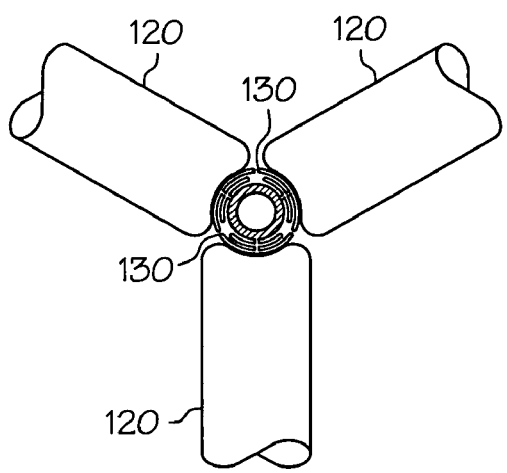
FIG. 30 shows the balloon catheter assembly of FIG. 29 with the antenna structures wrapped about the balloon.
Figure 31:
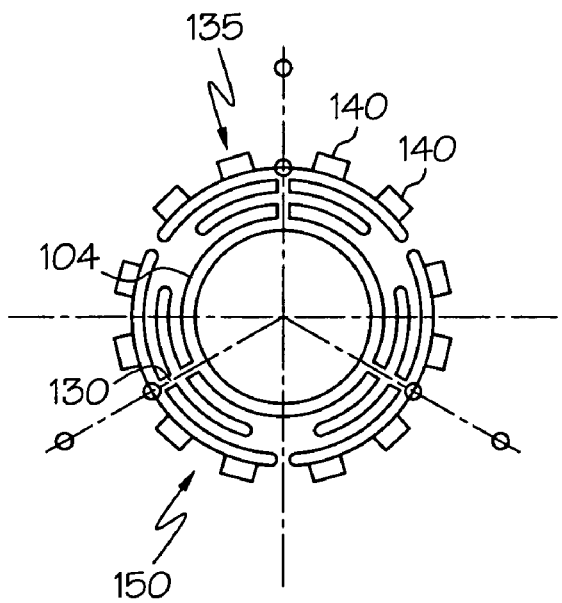
FIG. 31 shows an inventive balloon with a stent disposed thereabout.
Figure 32:
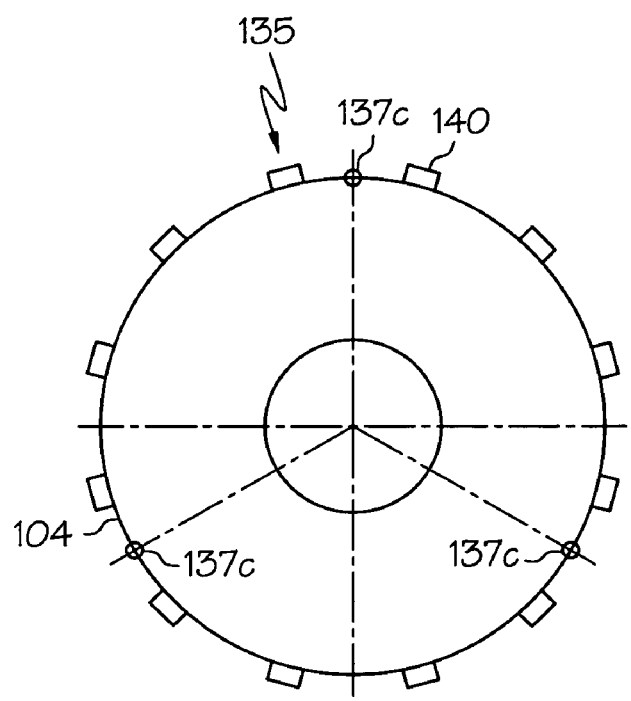
FIG. 32 shows the balloon and stent of FIG. 31 following expansion of both the balloon and stent.

An inventive balloon with three antenna structures is shown in FIGS. 30 and 31. Balloon 104 of FIG. 31 further comprises stent 135 having a plurality of struts 140 disposed thereabout. Upon expansion of balloon 104 and stent 135, the stent remains in contact with the same points on the balloon it was in contact with prior to expansion of the balloon and stent. As shown in FIGS. 31 and 32, stent 135 contacts balloon 104 at points of contact 137a, 137b and 137c both prior to and following expansion of the balloon and stent.

The inventive methods disclosed herein may further comprise a heat-set step to facilitate retention of the fold pattern produced by the process. Also, the inventive methods disclosed herein may optionally further comprise the step of disposing a balloon protector about the balloon to assure that the balloon does not unwrap. An example of a balloon protector is disclosed in U.S. Pat. No. 5,893,868. The inventive methods may further comprise one or more steps of coating the balloon with a desired coating. Suitable coatings include retraction coatings such as those disclosed in U.S. Pat. No. 5,490,839, and U.S. Pat. No. 5,738,901 and lubricity coatings such as those disclosed in U.S. Pat. No. 6,176,849.

Any of the inventive methods disclosed herein optionally may further comprise the step of disposing a prosthetic device about the medical balloon. Desirably, the prosthetic device is a stent. More desirably, the stent includes a coating such as, for example, those coatings disclosed below.

The invention is also directed to medical balloons formed by using any of the inventive balloon configuring methods disclosed herein as well as to the balloons described herein in their various configurations.

An inventive apparatus suitable for preparing some of the inventive medical balloons described herein is disclosed below.

In another embodiment, the invention is also directed to the combination of a medical balloon and an expandable prosthetic device disposed about the medical balloon where the medical balloon comprising a plurality of wings extending from a main balloon body. The wings are wrapped about the main balloon body such that upon inflation of the medical balloon there is substantially no relative rotational movement between the prosthetic device and the balloon. An example of such a combination is shown at 150 in FIG. 31.

The inventive balloon disclosed herein, in many of its embodiments, has a profile that is closer to circular than existing wrapped balloons. This feature results in less damage to the balloon during crimping of a stent disposed thereabout.

The invention is further directed to the combination of an inventive medical balloon such as those disclosed herein and a prosthesis, such as, for example, a stent, with the prosthesis disposed about the medical balloon. Desirably, the prosthesis includes a coating, desirably comprising a therapeutic agent. The term therapeutic agent is intended to include drugs, non-genetic therapeutic agents, genetic materials, cells.

Suitable coatings include polymer coating materials such as polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (BAYHDROL®, etc.), fibrin, collagen and derivatives thereof, polysaccharides such as celluloses, starches, dextrans, alginates and derivatives, hyaluronic acid, squalene emulsions, polyacrylic acid, available, for example, as HYDROPLUS® (Boston Scientific Corporation, Natick, Mass.), and described in U.S. Pat. No. 5,091,205, the disclosure of which is hereby incorporated herein by reference. Desirably, the coating may be a copolymer of polylactic acid and polycaprolactone.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation, the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Dimeric proteins such as BMP-2, BMP-3, BMP-4, BMP-5, BMP-6 and BMP-7 can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cells can be of human origin (autologous or allogeneic) or from an animal source (xenogeneic), or genetically engineered if desired to deliver proteins of interest at the transplant site. The delivery media can be formulated as needed to maintain cell function and viability.

Other suitable therapeutic agents include antibiotics and radioactive coatings.

The invention is also directed to an apparatus for configuring a medical balloon of a medical balloon catheter assembly. The apparatus comprises a catheter holder, a plurality of movable blades disposed about a common central point and one or more blade moving devices in mechanical communication with the movable blades, the one or more blade moving devices is capable of moving the movable blades inward toward the common central point.

An example of an inventive balloon configuring apparatus is shown schematically at 200 in FIGS. 33-36. Apparatus 200 comprises a catheter holder 204, at least one and desirably a plurality of impinging members 114 and a means for moving the impinging members. The catheter holder may be of any suitable configuration and size to satisfactorily position and retain the catheter.

Figure 33:
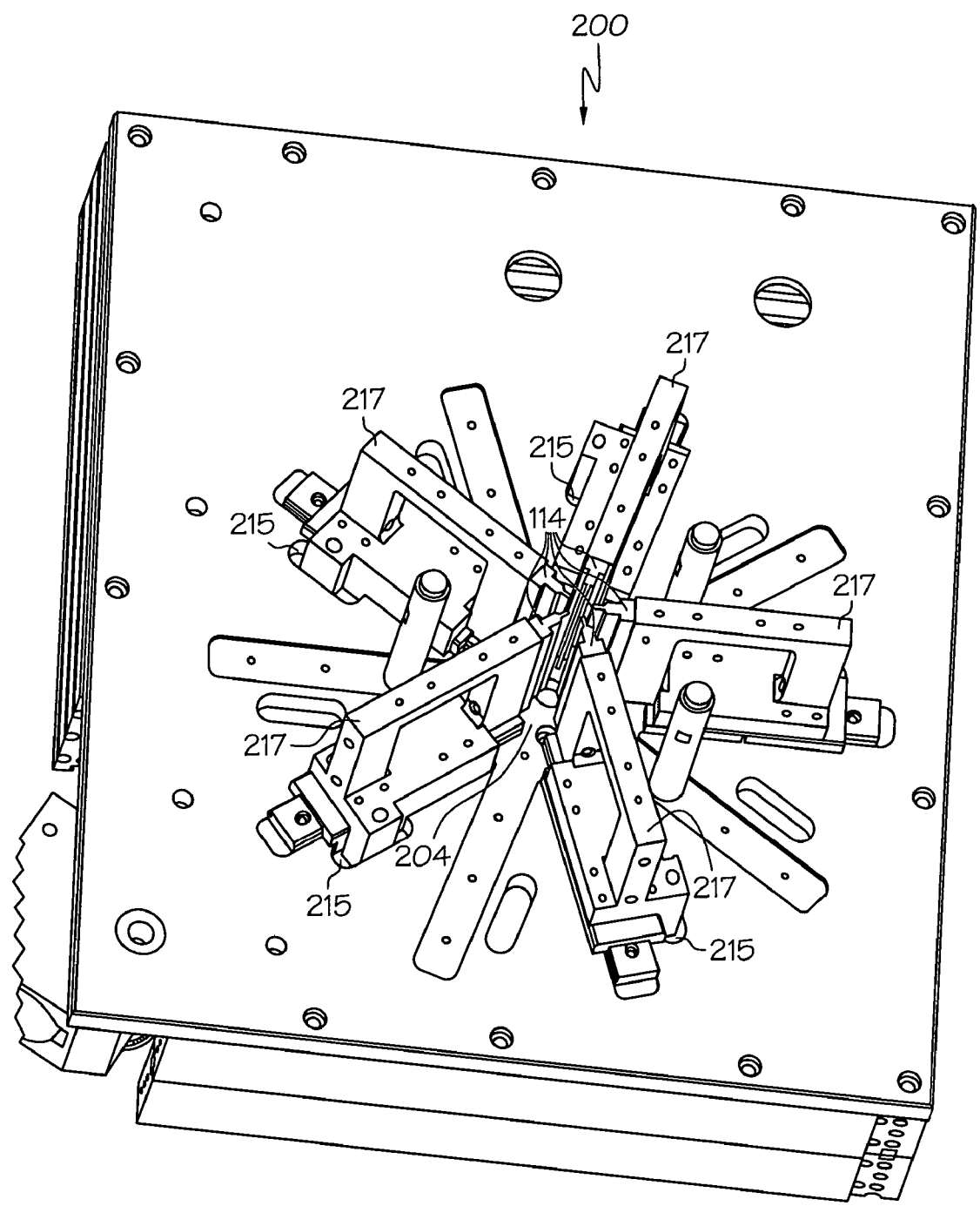
FIG. 33 shows a top down perspective view of an inventive balloon configuring device.
Figure 34:
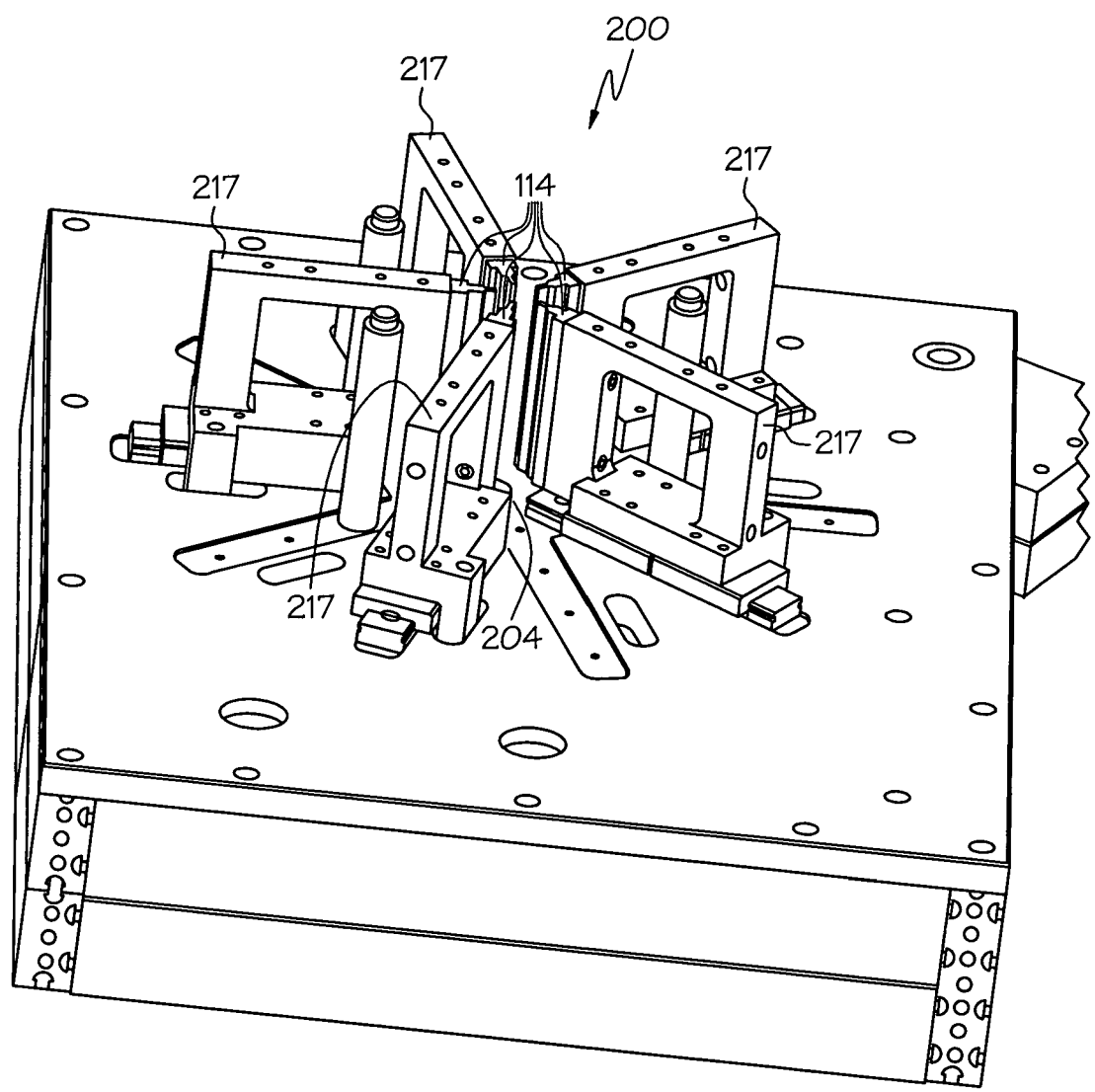
FIG. 34 shows an alternate side perspective view of the inventive balloon configuring device shown in FIG. 33.
Figure 35:
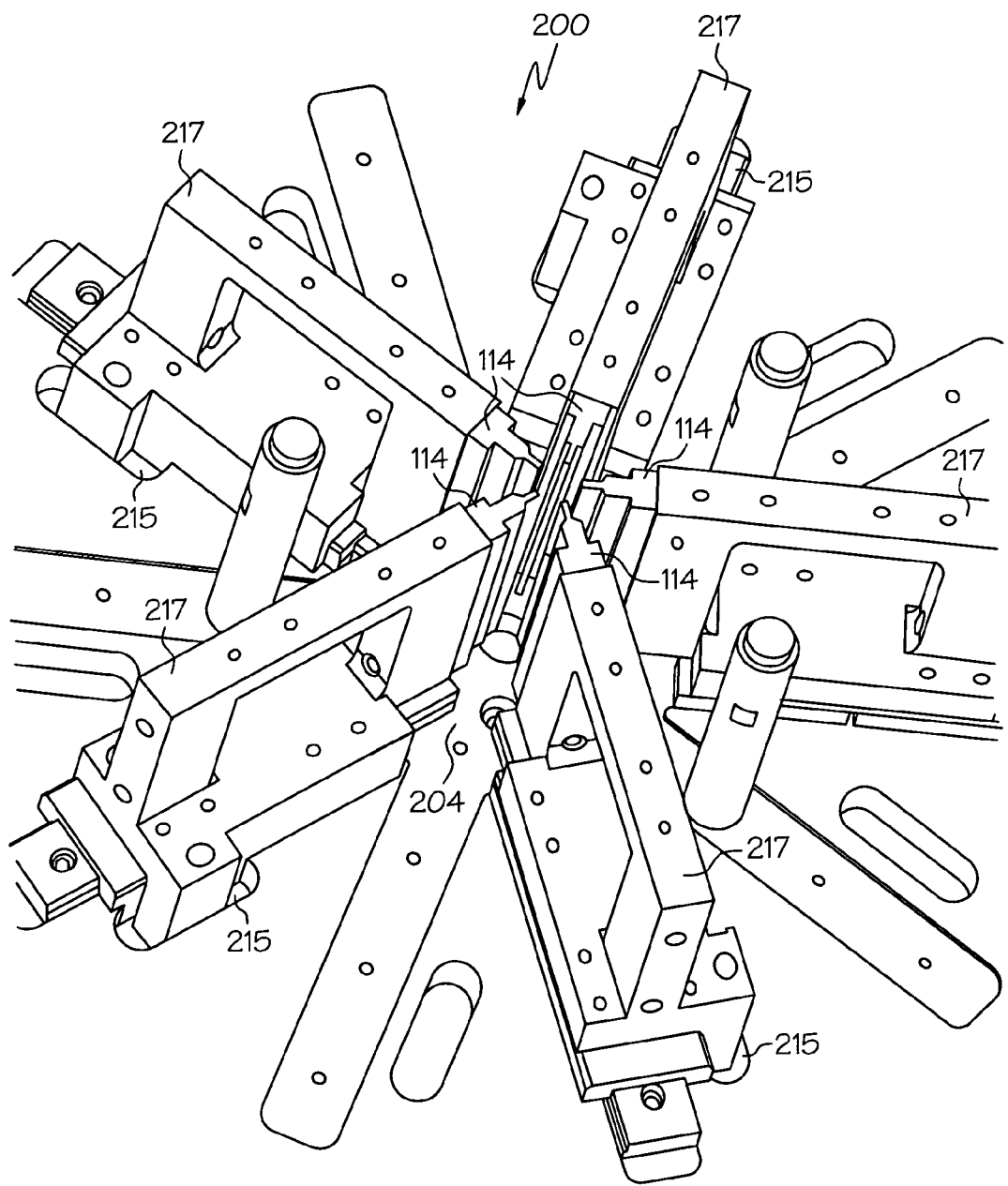
FIG. 35 is a perspective view of the front of the balloon configuring device shown in FIGS. 33 and 34.

As shown by way of example in FIG. 33, the means for moving the impinging members, as shown in FIG. 36 is in the form of a circular plate 213 with a plurality of openings 215 therethrough. Openings 215 are arcuate and angle radially inward. Each impinging member 114 extends from an arm 217 which, in turn, has a circular knob 219 extending therefrom as shown in FIG. 36. Each knob 219 is disposed in an opening 215. The knob and opening are sized such that the knob engages the inner walls of the opening.

Circular plate 213 is rotatably associated with support 221 via a cam shaft (not shown) using any means known in the art. Circular plate 213 may be rotated using any means known in the art. One example is a linear actuator device or a piston system for driving a cam. Shown in this embodiment is a linear actuator mount 225 is fixedly attached to support 221 and includes a coupling 227 for a linear actuator (not shown) for driving the cam which in turn rotates the circular plate 213. A bearing housing 223 is mounted on support 221 whereby the cam shaft is adapted to rotate relative to the bearing housing 223. As the linear actuator is driven forward or backward, the cam shaft rotates causing the circular plate 213 to rotate in a first direction or in a second, opposite direction causing arms 217 and impinging members 114 to move radially inward or outward depending on the direction of rotation of the circular plate.

Such assemblies for moving the impinging members is described above by way of example only and are well known to those of skill in the art. Any other suitable device for moving the impinging members may also be used including a piston system.

Figure 38:
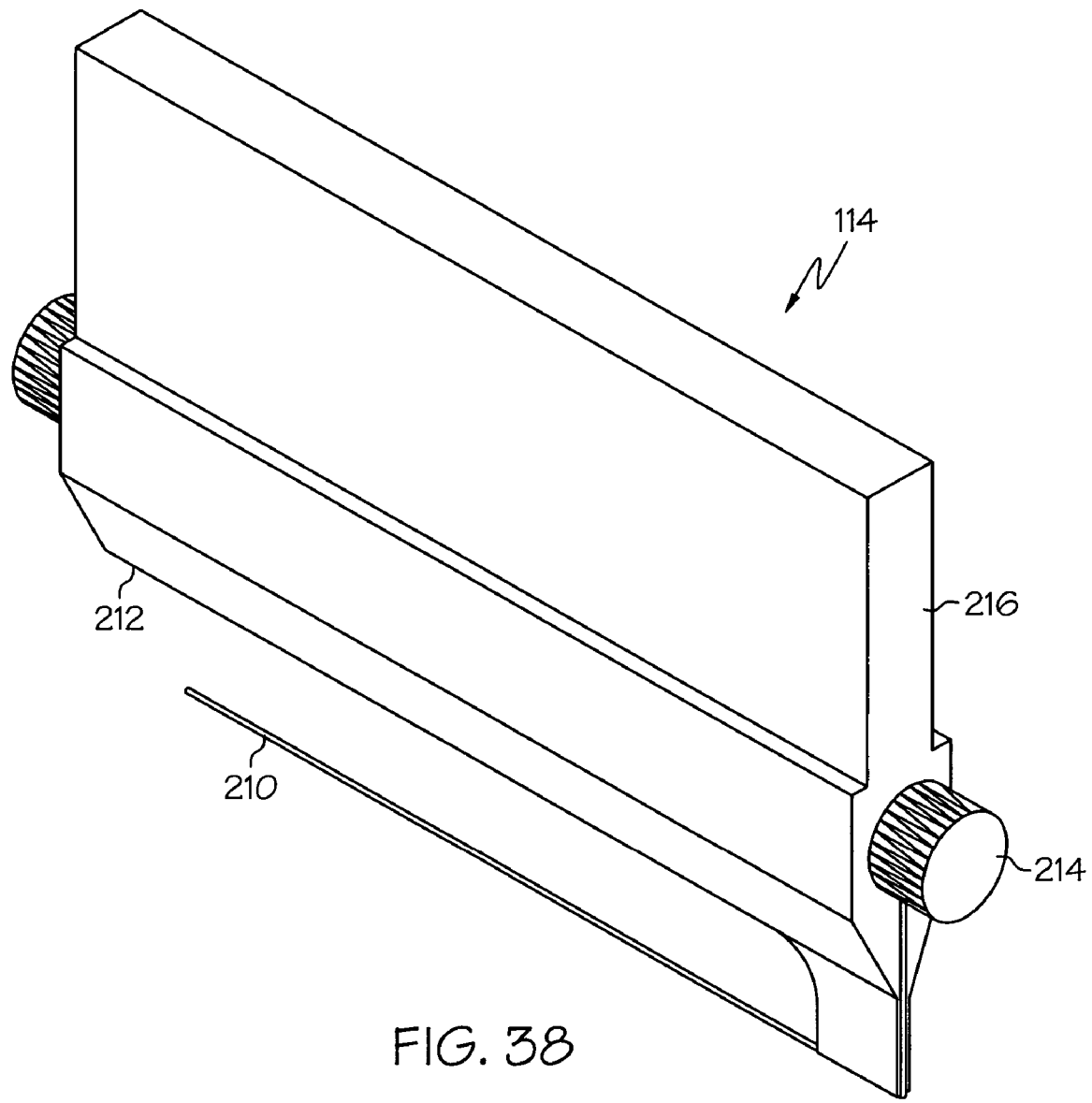

Impinging members 114, as shown in greater detail in FIG. 37 and FIG. 38, are in the form of a tensioned line 210 which is held by line holder 212 which extend from body 216. Typically, the tension of the line may be adjusted by turning knob 214 clockwise or clockwise to increase or decrease the tension of the member. Desirably, the line is provided in the form of a smooth metal wire to avoid damaging the balloon. Other suitable materials include polymeric cables. By way of non-limiting example, a polyamide based cable may be used. The embodiment of the impinging member of FIG. 37 differs from the embodiment of FIG. 38 in that line 210 as shown in FIG. 38 is supported only at a single end. In the embodiment of FIG. 38, the line will typically be in the form of a rigid polymeric material.

Figure 39:
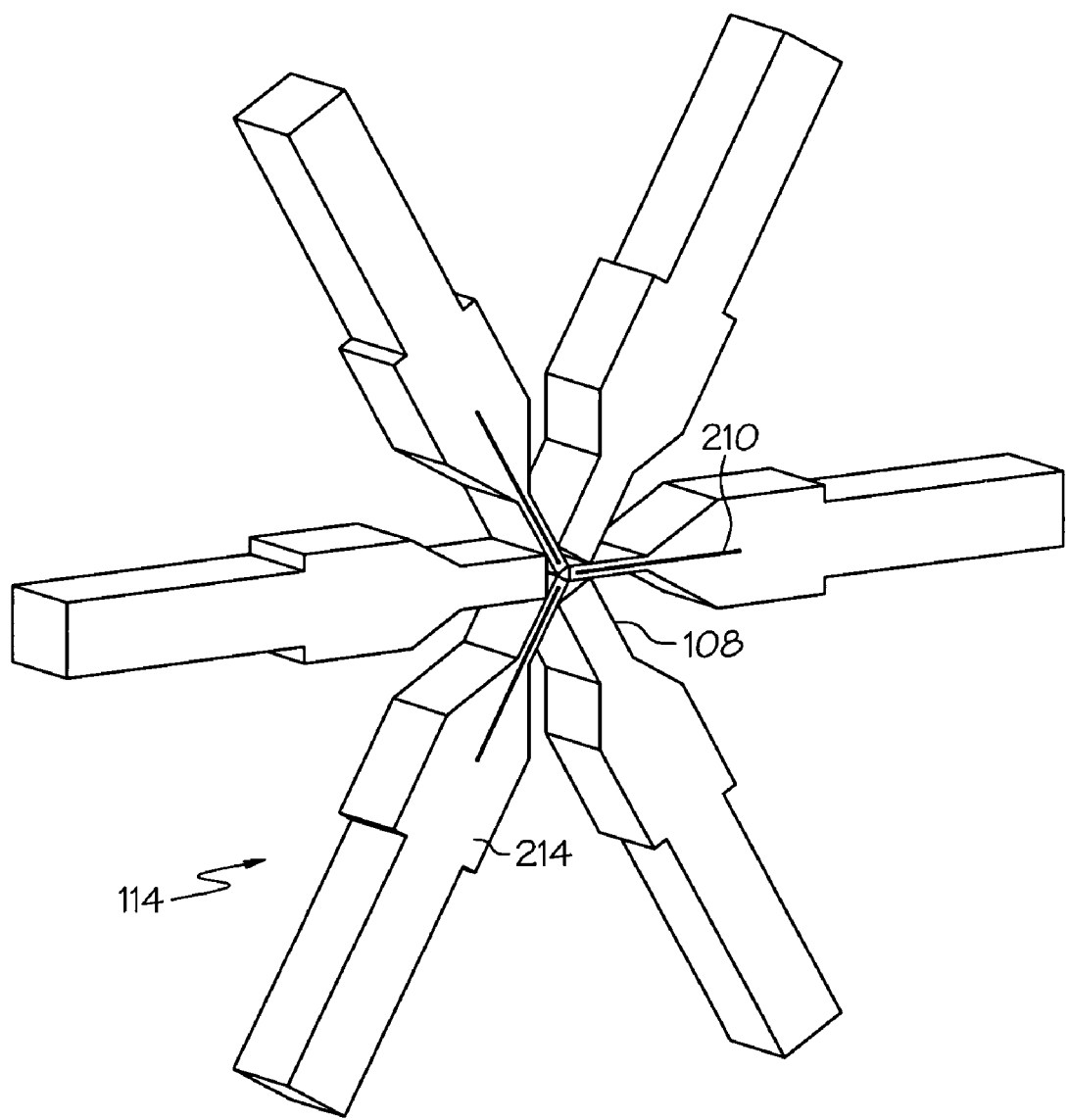
FIG. 39 shows a perspective view of an arrangement of impinging members.
Figure 40:
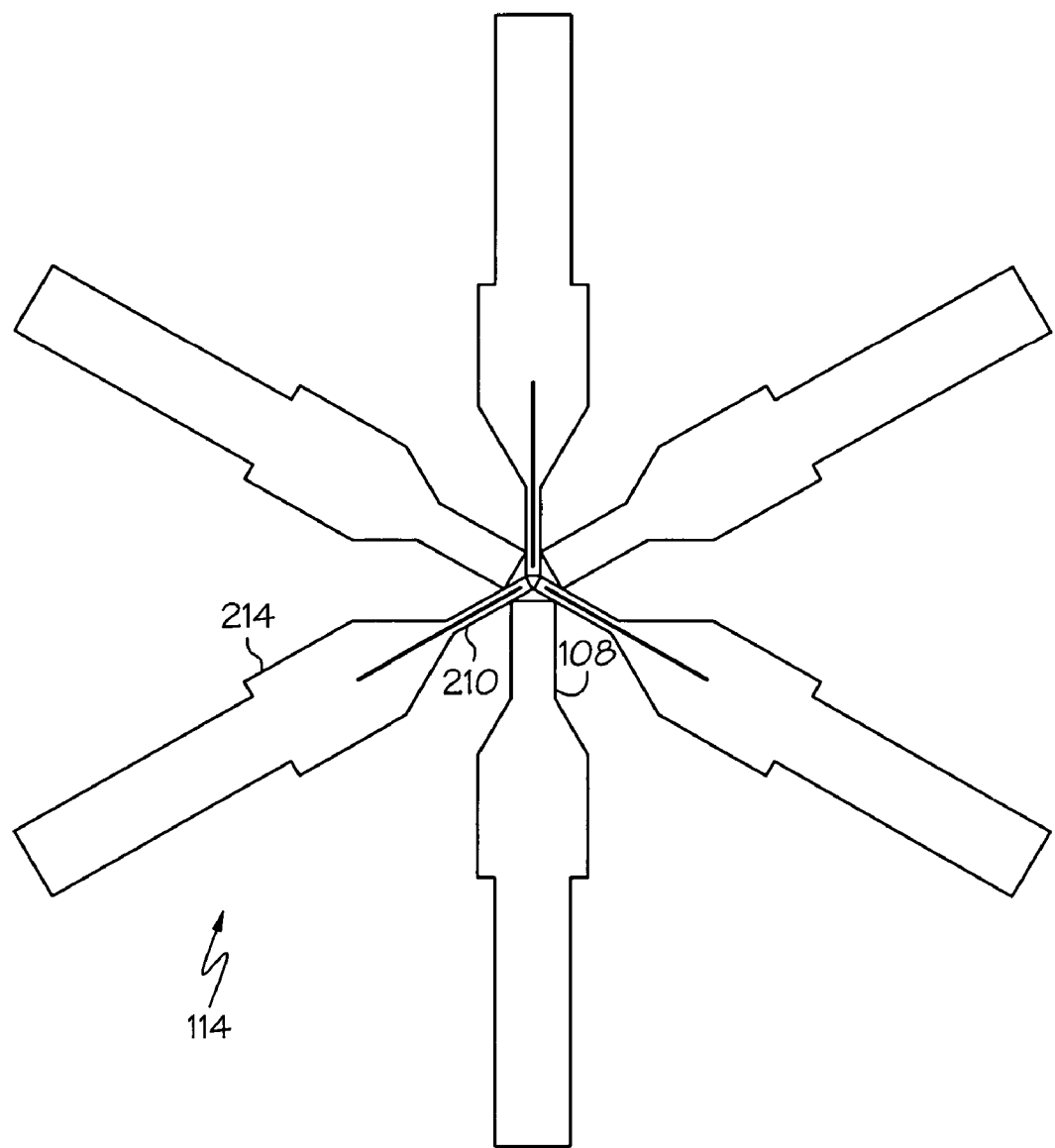
FIG. 40 shows a side view of an arrangement of impinging members.

Impinging members 114 are shown in an arrangement along with impinging members 108 in perspective view and in side view in FIGS. 39 and 40. Impinging members 108 have a relatively wide balloon contacting surface as compared with impinging members 114. Any suitable material may be used for impinging members 108 including polymeric materials and metals. The balloon contacting surface of the impinging member should be smooth to avoid damaging the balloon.

Figure 41:
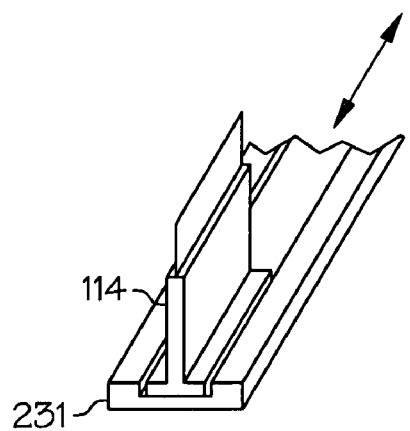
FIG. 41 shows a slidable impinging member.

The impinging members 108 and 114 of device 200 operate in unison. Inventive balloon configuring devices may also be provided in which impinging members 108 are controlled independently of impinging members 114. This may be accomplished by driving each of the impinging members shown in FIGS. 39 and 40 with a piston (not shown). The pistons driving impinging members 108 would be controlled independently of the pistons driving impinging members 114. A balloon configuring device may also be provided where each of the impinging members is independently movable, such as with independently controlled pistons. The device may also be configured so that each of the pistons may be slidable along a track. FIG. 41 is a schematic illustration showing impinging member 114 mounted on track 231 allowing for the impinging member to be withdrawn not only in a radial direction but also in an axially direction.

Figure 42:
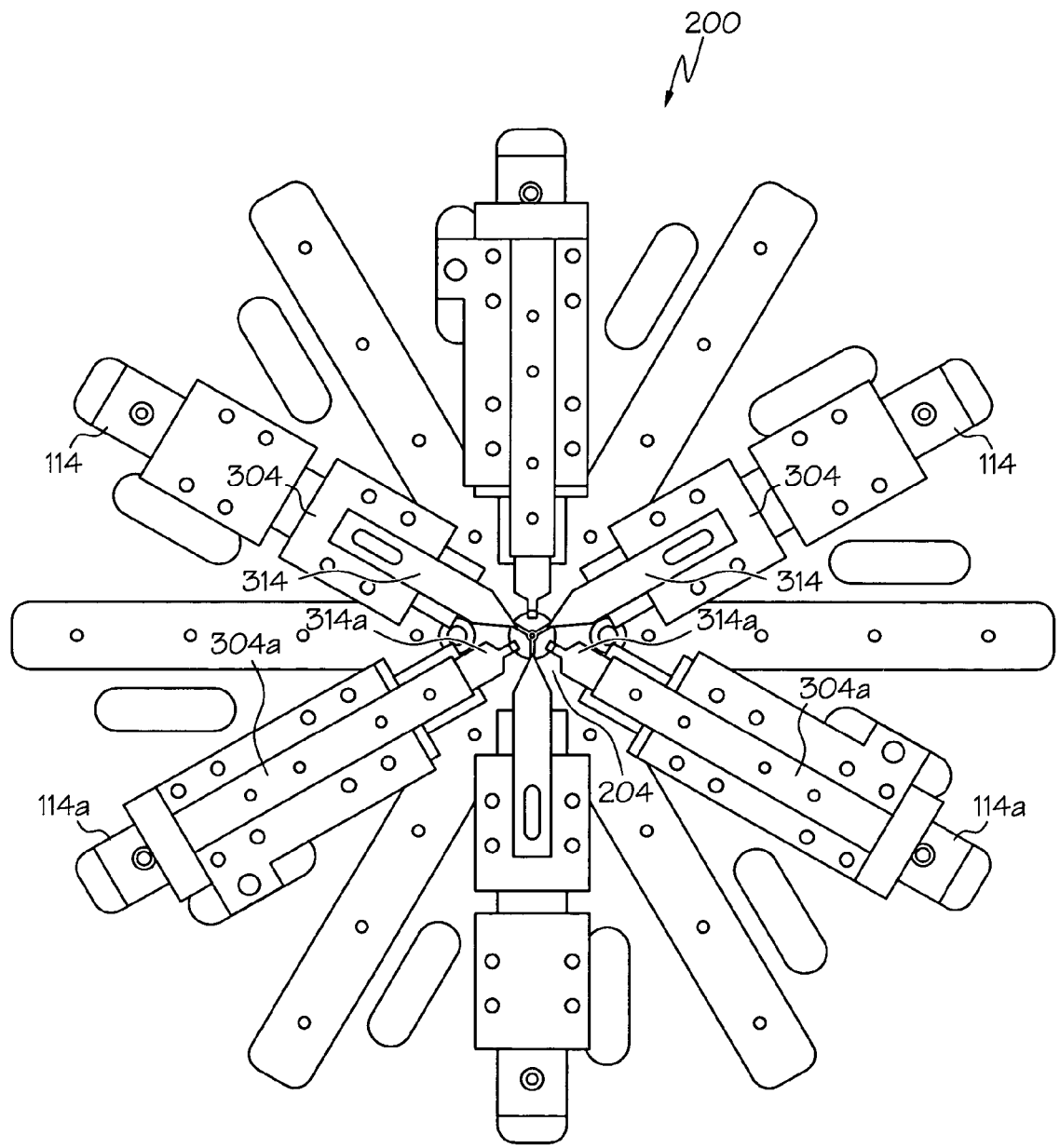
FIG. 42 shows an embodiment of a balloon folding apparatus according to the present application.

Another example of an inventive balloon configuring apparatus is shown schematically at 200 in FIG. 42. The apparatus shown generally at 200 includes a catheter holder 204 which may be of any suitable configuration and size to satisfactorily position and retain the catheter, and a first set of impinging members 114 having a conical or V-shaped soft tip construction 314 connected to a body portion 304 and a second set of parallel impinging members 114a having a flat edged soft tip construction 314a connected to a body portion 304a, and a means for moving the impinging members. The first set of impinging members 114 form first wings upon manipulation of the balloon, and the second set of impinging members 114a forms secondary T-shaped wings upon manipulation of the first wings. Desirably, the balloon will be reinflated at least to a partially inflated state thus forming lobes or smaller balloon portions prior to manipulation to form the T-shaped wings as described above and as represented by FIGS. 8-19.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 1; claim 4 may be taken as alternatively dependent on claim 2, or on claim 1; claim 5 may be taken as alternatively dependent on claims 1, 2, or 3; etc.).

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of configuring a medical balloon catheter assembly comprising the steps of:
   providing a medical balloon catheter assembly including a medical balloon;
   at least partially inflating the medical balloon;
   forming a plurality of primary wings in the balloon, the primary wings spaced about the periphery of the balloon and extending from a central portion of the balloon;
   deflating said medical balloon;
   at least partially reinflating the medical balloon such that the primary wings form lobes;
   manipulating the lobes; and
   deflating said medical balloon to form a T-shaped wings from each of the primary wings.

2. The method of claim 1 wherein a vacuum is applied to said balloon during deflating said balloon.

3. The method of claim 1 wherein the primary wings and the T-shaped wings are formed by impinging members which are directed radially inward to apply a radially inward force to the balloon at a plurality of locations.

4. The method of claim 1 wherein the primary wings are formed by providing a set of first impinging members spaced about the periphery of the balloon and wherein the primary wings are formed by directing the plurality of first impinging members radially inward to apply a radially inward force to the balloon at a plurality of locations and the T-shaped wings are formed by providing a plurality of second impinging members spaced about the periphery of the balloon and wherein the T-shaped wings are formed by directing the plurality of second impinging members radially inward to the lobes to apply a radially inward force to the primary lobes.

5. The method of claim 4 wherein the first impinging members have a conical tip which comes into contact with the balloon.

6. The method of claim 4 wherein the second impinging members have a flat edge which comes into contact with the balloon.

7. The method of claim 4 wherein said first impinging members, said second impinging members or both have a soft tip.

8. The method of claim 7 wherein the soft tip is polymeric.

9. The method of claim 7 wherein said soft tip is silicone.

10. The method of claim 1 further comprising the step of wrapping the T-shaped wings about the central portion of the balloon.

11. The method of claim 10 further comprising the step of disposing a balloon protector about the balloon after wrapping.

12. The method of claim 11 wherein the balloon protector is a bi-tube.

13. The method of claim 1 wherein at least three T-shaped wings are formed.

14. The method of claim 1 wherein the primary wings are formed by impinging one or more first impinging members inward against the balloon while deflating said balloon and the T-shaped wings, at least partially reinflating the balloon and then forming the T-shaped wings by impinging two or more second impinging members inward against each primary wing, and deflating said balloon.

15. The method of claim 1 wherein each T-shaped wing is formed from one primary wing after said primary wing is reinflated to a lobe.

16. The method of claim 1 wherein a vacuum is applied during deflating said balloon.

17. The method of claim 1, wherein, subsequent to the deflating step, the medical balloon has a contracted condition and is expandable to an expanded condition, when the medical balloon is in its expanded condition, the central portion of the medical balloon has a circular cross-section.

18. A method of forming balloon wings in a medical balloon comprising the steps of:
    providing a medical balloon;
    inflating said medical balloon;
    forming one or more primary lobes therein, the primary lobes spaced about the periphery of the balloon and extending from a central portion of the balloon;
    forming a plurality of secondary lobes from each primary lobe by applying an inward force to each of the primary lobes, the inward force applied by impinging members, the impinging members comprising a soft-tipped structure; and
    deflating the balloon.

19. The method of claim 18 wherein the inward force is applied to the primary lobes via a plurality of impinging members.

20. The method of claim 19 wherein the impinging members are removed following the forming step by moving the impinging members in an axial direction.

21. The method of claim 18 further comprising the step of wrapping said secondary lobes about the central portion of the balloon.

22. The method of claim 21 further comprising the step of disposing a balloon protector about the balloon after wrapping.

23. The method of claim 22 wherein said balloon protector is a bi-tube.

24. The method of claim 18 wherein, upon the deflating of the balloon, an antenna-shaped structure is formed from each of the plurality of secondary lobes from each primary lobe.

25. The method of claim 18, wherein, subsequent to the deflating step, the medical balloon has a contracted condition and is expandable to an expanded condition, when the medical balloon is in its expanded condition, the central portion of the medical balloon has a circular cross-section.

26. A method of forming balloon wings in a medical balloon comprising the steps of:
provuding a medical balloon in a deflated configuration with two or more primary wings; and
forming a T-shaped wing from each primary wing by applying an inward force to each of the primary wings; and
deflating the balloon, such that the T-shaped wings are deflated and are circumferentially spaced around the balloon.

27. The method of claim 26 further comprising the step of inflating the balloon prior to formation of the primary wings.

28. The method of claim 27 wherein the primary wings are formed by application of an inward force.

29. The method of claim 28 wherein the inward force is applied by first impinging members which contact the balloon.

30. The method of claim 29 wherein the impinging members have a conical shaped tip which contacts said balloon.

31. The method of claim 30 wherein the impinging members have a soft tip.

32. The method of claim 31 wherein the soft tip is polymeric.

33. The method of claim 31 wherein the soft tip is silicone.

34. The method of claim 30 wherein said second impinging members are different than said first impinging members.

35. The method of claim 34 wherein said second impinging members have a flat edged tip that comes into contact with said balloon.

36. The method of claim 29 wherein said T-shaped wings are formed by second impinging members.

37. The method of claim 36 wherein the impinging member has a soft-tipped structure.

38. The method of claim 37 wherein the soft-tipped structure is polymeric.

39. The method of claim 37 wherein the soft-tipped structure is silicone, polyurethane, polyolefin, metal or some combination thereof.

40. The method of claim 26 wherein said medical balloon is at least partially inflated prior to formation of said plurality of T-shaped wings.

41. The method of claim 26 wherein said medical balloon has three or more primary wings.

42. The method of claim 26 wherein said T-shaped wings are formed by impinging members.

43. The method of claim 26 wherein each T-shaped wing extends from a central portion of the balloon.

44. The method of claim 43 further comprising the step of wrapping the T-shaped wings around the central portion of the balloon while the balloon is deflated.

45. The method of claim 44 further comprising the step of disposing a balloon protector about said balloon after wrapping.

46. The method of claim 45 wherein said balloon protector is a bi-tube.

47. A medical balloon formed according to the method of claim 26.

48. The medical balloon of claim 47 in combination with a stent.

49. The medical balloon of claim 48, said stent further comprising a therapeutic agent.

50. The method of claim 26, wherein, subsequent to the deflating step, the medical balloon has a first end, a second end and a body portion longitudinally disposed between the first end and the second end, the medical balloon further having a contracted condition and being expandable to an expanded condition, when the medical balloon is in its expanded condition, the body portion of the medical balloon has a circular cross-section.

51. A method of configuring a medical balloon catheter assembly comprising the steps of:
providing a medical balloon catheter assembly including a medical balloon with one or more primary lobes therein;
forming a plurality of secondary lobes from each primary lobe by applying an inward force to each of the primary lobes;
deflating the balloon;
wrapping said secondary lobes about a central portion of the balloon; and
disposing a balloon protector about said balloon.

52. The method of claim 51 wherein said balloon protector is a bi-tube.

53. The method of claim 51 further comprising the steps of:
at least partially inflating the medical balloon; and
forming a plurality of primary lobes in the balloon, the primary lobes spaced about the periphery of the balloon and extending from a central portion of the balloon prior to providing said medical balloon catheter assembly.

54. The method of claim 51 wherein, upon the deflating of the balloon, an antenna-shaped structure is formed from each of the plurality of secondary lobes from each primary lobe.

55. The method of claim 51, wherein, subsequent to the deflating step, the medical balloon has a contracted condition and is expandable to an expanded condition, when the medical balloon is in its expanded condition, the central portion of the medical balloon has a circular cross-section.

* * * * *